United States Patent [19]

Lundgren et al.

[11] Patent Number: 4,746,293

[45] Date of Patent: May 24, 1988

[54] CONNECTING DEVICES

[76] Inventors: Dan Lundgren, Kyrkvägen 5, S-430 80 Hovås; Izidor Brajnovi, Narvavägen 10C, S-552 59 Jönköping, both of Sweden

[21] Appl. No.: 907,914

[22] Filed: Sep. 16, 1986

[30] Foreign Application Priority Data

Sep. 16, 1985 [SE] Sweden .............................. 8504275

[51] Int. Cl.⁴ .............................................. A61C 8/00
[52] U.S. Cl. .................................... 433/173; 433/169
[58] Field of Search ............... 433/168, 169, 173, 174, 433/175, 176

[56] References Cited

U.S. PATENT DOCUMENTS 4,178,686 12/1979 Riess et al. .......................... 433/173
4,626,214 12/1986 Artzl ................... 433/169

Primary Examiner—Robert Peshock
Attorney, Agent, or Firm—Pollock, Vande Sande & Priddy

[57] ABSTRACT

A connecting device is included in oral and extra-oral prostheses of the type which is partially implanted in bodily tissue, primarily bone tissue, by means of a specifically designed anchorage unit (a fixture). The connecting device provides more favorable stress and force distribution between the implanted and the outer portion of the prosthesis located peritissually. The connecting device includes an outer, cylindrical sleeve-shaped patrix (6) for connection to the outer prosthesis portion, for example by casting, and is designed to surround a central spacer screw (3) of a spacer (1) connected to the anchorage unit. The device connects through lower base (11), to a collar-shaped portion (4, 5) of the spacer (1) by the intermediary of a resilient member (7).

6 Claims, 1 Drawing Sheet

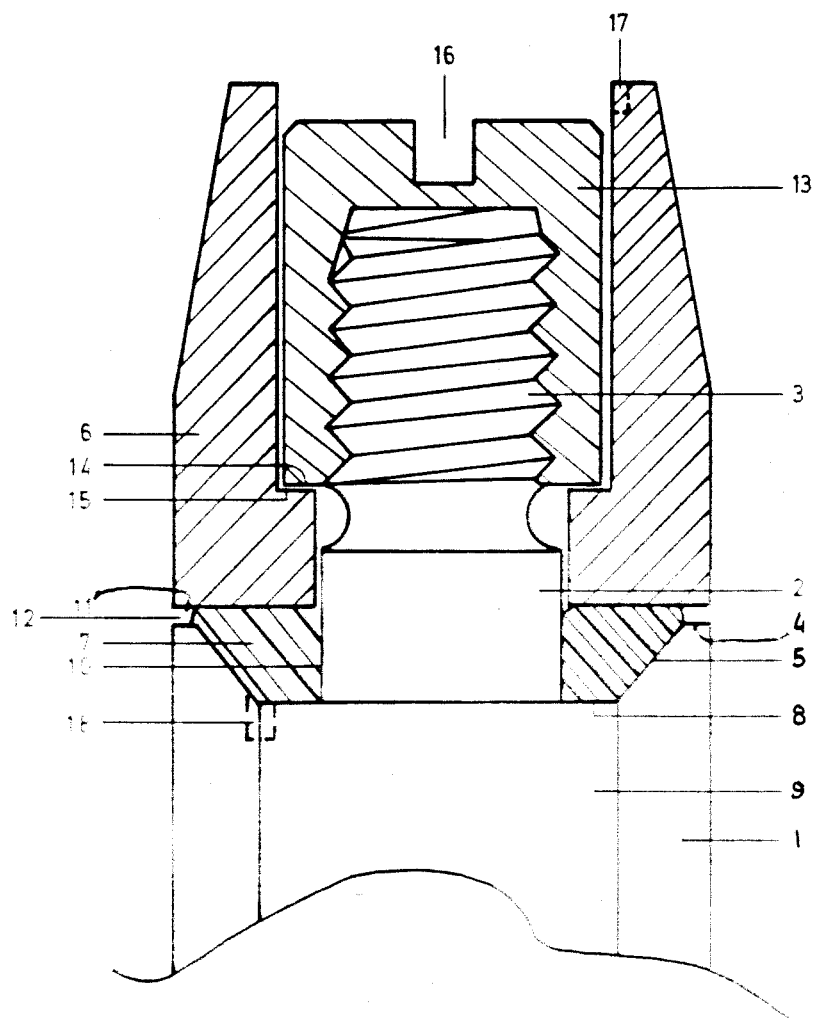

CONNECTING DEVICES

TECHNICAL FIELD

The present invention relates to a connecting device included in oral and extra-oral prostheses of the type which is partially implanted in body tissue, primarily in bone tissue, by means of a particularly designed anchorage unit (a fixture). The purpose of the present invention is to provide a connecting device, which would allow a more favorable stress and force distribution between the implanted and peri-tissual located portion of the prosthesis.

BACKGROUND ART

It is previously known in this Art to permanently anchor dental prostheses in the jawbone tissue. The method which has proved to result in the greatest anchorage stability—and the only method which has proved to afford a truly permanent anchorage in the bone tissue—is the so-called osseointegration method, developed by Professor Per-Ingvar Brånemark et, al. In Gothenburg, Sweden. The unique feature of this method is that the anchorage unit (the fixture) may be implanted, both very accurately and atraumatically, directly in the bone tissue without the necessity of interposed bonding tissue. This direct contact between fixture and bone tissue makes for optimum conditions for lasting healing by osseointegration.

The anchorage unit (the fixture) is in the form of a screw, preferably of titanium, and is implanted such that the upper portion of the screw is located flush with or slighly beneath the surface of the jawbone. This first operation is followed by a dentally unloaded healing period of a critical length, during which the screw is covered by intact mucosa. During this healing phase, the bone tissue grows onto and forms a unit with the implanted fixture. in the subsequent operation, the fixture is exposed and a spacer, also preferably made of titanium, is disposed on the fixture by means of a spacer screw. The dental prosthesis in the form of a crown or bridge construction is then anchored in place by means of a locking screw which in turn positionally fixes the spacer screw. This method has been successfully employed clinically for 20 years in conjunction with jawbone-anchored bridge constructions, and development is now underway concerning the anchorage of prostheses to other parts of the skeleton (extra-oral prostheses).

The unique properties of this method thus derive from the fact that the fixture is wholly incorporated in the bone tissue. This implies that the dental prosthesis will be relatively rigidly anchored in the jawbone, as opposed to, for example, the natural tooth which is more elastically supported. Such a rigid anchorage entails that the oral functional stresses are transmitted without attenuation to the dental prosthesis (the crown or bridge construction) and its anchorage (the spacer and the fixture), which may give rise to excessively high stresses in both the bone tissue anchorage and in the different components of the dental prosthesis. Even if the osseointegration method possesses uniquely advantageous properties as regards the risk of disengagement arising out of overloading, it is, of course nevertheless desirable to reduce, as far as is possible, the levels of force stresses. As a result, fracture of the prosthesis components can be avoided, at the same time as these may be dimensioned in such a manner as requires as little space as possible.

Concerning the oral functional and mastication forces, the velocity of forces and the mass involved are so insignificant that the damping effect of the elastic suspension on transmission of energy per unit of time should be of but marginal importance. Of considerably greater importance is the deflection which may be realized by elastic suspension of one or more (individual or interconnected) jawbone-anchored crowns in residual bite with natural teeth. Depending upon the degree of elasticity and, thereby, deflection, the occlusal forces can be distributed between the jawbone-anchored units and the natural teeth in a controllable manner. A harmonically adapted degree of elasticity might well also contribute to an optimum level of oral comfort for the patient.

In those cases where one or more jawbone-anchorer units are connected to the natural teeth of the residual bite, a pattern of deflection of the jawbone-achored unit or units which nicely approximates that of the natural teeth should be striven for. Probably, this will result in a considerably more favorable stress distribution throughout both the jawbone-anchored fixtures and across the superstructure/bridge construction which is connected between the fixture and the natural teeth.

Even in those cases where a bridge construction is anchored in the jawbone of a completely edentulous jaw, there may be a need to increase the patient's oral comfort by means of a gentler, less inflexible, occlusion realized by means of an elastic element.

Also in extra-oral prostheses, for example joint prostheses, there is a need in this Art for a more elastic suspension of the prostheses in order to increase the feeling of comfort and, above all, to make for a greater degree of inherent margin to destructive energy transmission level in that the elastic suspension, by deflection, on the one hand automatically leads to less force absorption over the region of the prosthesis and, instead, greater force is absorbed by, for example, the natural extremities, and, on the other hand considerably retards the velocity of the applied force. The possibility of elastic deflection also increases the time margin for the onset of the reflex protective reactions of the organism.

OBJECT OF THE PRESENT INVENTION

Hence, the object of the present invention is to realize a connecting device which, on the one hand, reduces the velocity of force on its application and, on the other hand, contributes to a more favorable distribution of applied forces and stresses on the bone-anchored prosthesis and natural, force-absorbing structures.

The invention is characterised in that the connecting device comprises an outer, sleeve-shaped patrix for connection to the outer prosthesis portion, for example by casting, which is so designed as to surround a central spacer screw of the spacer connected to the anchorage unit, and connects, with its base, to a collar-shaped portion of the spacer by the intermediary of a resilient member.

In one advantageous embodiment of the present invention, the patrix and the spacer are designed such that an annular space is formed between the base surface of the patrix and adjacent surfaces of the spacer screw and the spacer which accommodate the resilient member. This suitably consists of an O-ring of rubber, but may also comprise an appropriate metal material.

BRIEF DESCRIPTION OF THE ACCOMPANYING DRAWING

The present invention will be described in greater detail hereinbelow, with reference to the accompanying Drawing which shows one example in cross-section of how the connecting device according to the invention may be designed for connection to an extant, standard spacer. In such instance, the connecting device may be utilized both for individual jawbone-anchored crowns in residual bite with or without connection to the patient's own teeth, and for bridge constructions with or without residual bite connection. It may also, naturally, be utilized for extra-oral prostheses with osseointegrated or other anchorage units.

DESCRIPTION OF PREFERRED EMBODIMENT

Referring to the Drawing, the upper portion of a spacer 1 is shown, which is disposed on an anchorage unit—a fixture—(not shown) implanted in jawbone tissue. The spacer 1 is provided with a central, cylindrical spacer screw 2 designed specifically for this purpose with an extended, exteriorly threaded pin 3. The spacer 1 is provided with a collar consisting of two surfaces: an outer horizontal surface 4 and an obliquely inclined surface 5 located inside the surface 4.

Such spacers are per se previously known and will not, therefore, be described in greater detail here.

With the intention of obtaining a more favorable force transmission between the anchorage unit and the outer prosthesis portion, a connecting device in the form of an outer, sleeve-shaped patrix 6 is connected to the spacer. The outer circumferential surface of the patrix connects to the outer prosthesis portion, for example by casting, and the patrix is so designed that it surrounds the central spacer screw 2, 3. The base of the patrix connects to the collarshaped portion 4, 5 of the spacer by the intermediary of a resilient member 7 in the form of an O-ring of high-quality rubber, for example EPDM (ethylene-propylene) rubber. The spacer and the spacer screw are preferably made of titanium, while the patrix 6 is suitably made of dental gold.

The obliquely inclined surface 5 of the collar-shaped portion of the spacer forms, together with an upper horizontal surface 8 on a cuff 9 of the spacer, two of the walls of an annular tunnel for the resilient member 7, namely the lower horizontal wall and the oblique lateral wall. The remaining walls of the annular tunnel viz. the medial, vertical wall 10 and the upper horizontal wall 11 are formed by the circumferential surface of the spacer screw, which in this case is of circular profile, and the planar, lower base surface of the patrix 6, respectively.

The annular tunnel of rhomboid cross-section which is formed by the above-mentioned surface is adapted to the resilient member in the form of an O-ring of rubber. In this case, the O-ring is dimensioned to permit a deflection of the order of magnitude of about 100–200 μm. In eccentric or oblique loading, this corresponds to a maximum angular displacement of 1°–2°, which must be considered as fully satisfactory in view of possible connection to, for example, natural teeth.

The patrix surface 11 is so disposed as to depress the O-ring 7 and provide the contemplated elastic transmission of forces between the outer prosthesis portion and the spacer (the fixture). It should here be observed that the play 12 provided between the patrix surface 11 and the spacer collar surface 4 should exceed 200 μm in order to permit the planned elastic deflection of 100–200 μm.

The elastic connection is anchored (locked) by an interiorly threaded special nut 13 manufactured of, for example, gold. The nut is screwed onto the exteriorly threaded pin 3 of the spacer screw such that its lower peripheral end surface 14 meets a horizontal heel 15 on the patrix 6. The nut is screwed on so far that light compression of the O-ring is attained. This light compression or pre-tensioning may be exactly determined in that the screw slot 16 which is disposed in the top of the nut is turned so as to register with a groove 17 in the upper patrix edge. By provision of further two such groove markings in the patrix edge to which the screw slot can be turned, both moderate and hard pre-tensioning of the connecting device may be mode, depending upon the deflection amplitude which is deemed to be most purposeful in each individual situation.

The upper surface of the special nut may be covered with, for example, a gold washer once it has been locked by a droplet of acrylate. Acrylate is then applied over the gold washer in order to fill the aperture through which the nut was applied.

To prevent possible torsional forces from running up and disengaging the spacer screw 2 in cases of implant which comprise individual crowns, the spacer 1 and the spacer screw 2 may be provided with a milled groove 18 in which a droplet of acrylate can be applied for reversible locking.

Bench tests of prototypes of the connecting device with the above-disclosed components have shown that the deflection pattern fundamentally agrees with the deflection of, for example, a tooth, in other words such deflection is initially relatively great in relation to the applied force and logarithmically reduces on constant force increase. By governing the pre-tension of the connecting device, it is possible to determine at which level of force or at which moment of forces measurable deflection is to occur.

The present invention should not be considered as restricted to that described above and shown on the Drawing, many modifications being conceivable without departing from the spirit and scope of the appended claims.

What we claim and desire to secure by Letters Patent is:

1. A connecting device for dental prosthesis for connecting a first portion of a prosthesis partially implanted into body tissue to a second peri-tissual outer portion of the prosthesis, the first portion including an anchorage unit for implantation into tissue and a spacer having a lower collar-shaped part disposed on the anchorage unit and a screw member extending upwardly from the lower part, the lower collar-shaped part having a top surface including a horizontal portion and an inclined portion, said connecting device comprising:

an outer, cylindrical sleeve member having a top portion and a lower base, said sleeve having an outer surface for connection to an outer prosthesis portion, said sleeve member being inserted over the screw member, with the surface of said lower base facing the top surface of the collar-shaped part of the spacer and terminating at a distance therefrom to form an annular space therebetween;

means for securing said sleeve member to the spacer; and, a resilient member positioned within said annular space and substantially corresponding to the shape of said annular space for providing a better stress distribution between the implanted and peri-tissual outer portion of the prosthesis, said resilient member being dimensioned to provide a gap between said lower base surface of said sleeve and the horizontal portion of the top surface of the collar-shaped portion of the spacer.

2. The connecting device according to claim 1, wherein said means for securing includes a locking washer insertable on the threaded pin of the spacer screw, and an inwardly extending, annular heel on said sleeve member which cooperates with the lower, peripheral end surface of the locking washer for imparting light pre-tensioning to said resilient member.

3. The connecting device according to claim 1, wherein said annular space forms a tunnel of rhomboid cross-section corresponding to the shape of said resilient member.

4. The connecting device according to claim 1, wherein said resilient member includes an O-ring of rubber.

5. The connecting device according to claim 1, wherein said resilient member includes an O-ring of metal.

6. The connecting device according to claim 1, wherein the magnitude of the deflection of said resilient member is in the range of about 100 to 200 $\mu$m.

* * * * *